United States Patent [19]
Ambroziewigz

[11] Patent Number: 5,843,467
[45] Date of Patent: Dec. 1, 1998

[54] TOPICAL OINTMENT CONSISTING OF ANIMAL FAT, PLANTAIN LANCETOWATA, AND CALENDULA AND METHODS OF PRODUCING THE SAME

[76] Inventor: Wieslaw Ambroziewigz, 23 Doncaster Drive, Brampton, Ontario, Canada, L6T 1S8

[21] Appl. No.: 679,583

[22] Filed: Jul. 15, 1996

[51] Int. Cl.⁶ .................................................... A61K 7/00
[52] U.S. Cl. ...................... 424/401; 424/405; 424/195.1; 514/886; 514/887
[58] Field of Search ................................ 424/401, 195.1; 514/886, 887

[56] References Cited

U.S. PATENT DOCUMENTS

| | | | |
|---|---|---|---|
| 4,749,572 | 6/1988 | Ahari | 424/132 |
| 5,061,491 | 10/1991 | Deryabin | 424/195.1 |

*Primary Examiner*—Thurman K. Page
*Assistant Examiner*—D. Faulkner

[57] ABSTRACT

A composition for a topically healing ointment having all natural herbs and an animal fat base. The combination of which forms a salve that is active against one or a combination of sources of viral, bacterial and fungus infections that have the ability to penetrate beneath the epidermal layer of the skin.

4 Claims, No Drawings

TOPICAL OINTMENT CONSISTING OF ANIMAL FAT, PLANTAIN LANCETOWATA, AND CALENDULA AND METHODS OF PRODUCING THE SAME

BACKGROUND OF THE INVENTION

1. Field of the Invention

The present invention relates to a healing salve and more particularly pertains to a skin ointment composed of natural herbs for topical application to heal epidermal infections, and further relieve joint pain associated with fluid build-up.

2. Description of the Prior Art

The use of a topical ointment is known in the prior art. More specifically, topical ointments heretofore devised and utilized for the purpose of treatment of epidermal irritation are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,370,876 to Noll et al. discloses an antimicrobial protective skin composition and method for protecting skin from body fluids. U.S. Pat. No. 5,137,718 to Gillespie discloses an infection fighting composition for topical application. U.S. Pat. No. 4,879,116 to Fox, DeWitt and Rothenberger discloses a skin protein complexion composition for the potentiation of the substantivity of aluminum acetate through the use of a cationic emulsifier as an aide in skin healing. U.S. Pat. No. 4,654,211 to Ezaki, Hashikmoto, Komori, Umehara, and Kohoka discloses a new compound, F-900541 production and use thereof. Lastly, U.S. Pat. No. 4,364,929 to Sasmor and Rothwell discloses a germicidal colloidal lubricating gels and method of producing the same.

While these devices fulfill their respective, particular objectives and requirements, the aforementioned patents do not describe healing salve that allows an all natural ointment to aide in the healing of athletics foot, mycosis, shingles, psoriasis, boils, hemorrhoids, acne, while at the same time relieving pain associated with fluids on joints and knees; atheroma; and hair loss.

In this respect, the healing salve according to the present invention substantially departs from the conventional formulas and compositions of the prior art, and in doing so provides a product primarily developed for the purpose of a skin ointment composed of natural herbs for topical application to heal epidermal infections, and further relieve joint pain associated with fluid build-up.

Therefore, it can be appreciated that there exists a continuing need for a new and improved healing salve which can be used for a skin ointment composed of natural herbs for topical application to heal epidermal infections, and further relieve joint pain associated with fluid build-up. In this regard, the present invention substantially fulfills this need.

SUMMARY OF THE INVENTION

In view of the foregoing disadvantages inherent in the known types of topical ointments now present in the prior art, the present invention provides an improved healing salve. As such, the general purpose of the present invention, which will be described subsequently in greater detail, is to provide a new and improved healing salve and method which has all the advantages of the prior art and none of the disadvantages.

To attain this, the present invention essentially comprises salve for topical application to skin consisting essentially of fifty-five to seventy percent by weight of an animal fat having been extracted directly from the fatty tissue of an animal through heating; five to twenty percent by weight of a mixture of plantain; and five to ten percent by weight of a mixture of calendula.

The healing salve wherein the plantain being plantago major and plantago lancetowata. The healing salve having the ability to penetrate the human epidermis layer upon topical application for combating the infectious bacteria. The healing salve wherein the weight percent ratio between the animal fat and a mixture of the plantain and calendula is 7 to 2 to 1 or greater.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the formulation of other compounds, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved healing salve which has all of the advantages of the prior art topical ointments and none of the disadvantages.

It is another object of the present invention to provide a new and improved healing salve which may be easily and efficiently manufactured and marketed.

It is further object of the present invention to provide a new and improved healing salve which is a durable and stable composition.

An even further object of the present invention is to provide a new and improved healing salve which is susceptible of a low cost of manufacture with regard to both materials and labor, and which accordingly is then susceptible of low prices of sale to the consuming public, thereby making such healing salve economically available to the buying public.

Still yet another object of the present invention is to provide a new and improved healing salve which provides in the compositions and methods of the prior art some of the advantages thereof, while simultaneously overcoming some of the disadvantages normally associated therewith.

Even still another object of the present invention is to provide a healing salve for a skin ointment composed of natural herbs for topical application to heal epidermal infections, and further relieve joint pain associated with fluid build-up.

Lastly, it is an object of the present invention to provide a new and improved composition for a topically healing ointment having all natural herbs and an animal fat base. The combination of which form a salve that is active against one or a combination of sources of viral, bacterial and fungus infections that have the ability to penetrate beneath the epidermal layer of the skin.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the descriptive matter in which there is illustrated preferred combination of ingredients of the invention.

DESCRIPTION OF THE PREFERRED EMBODIMENT

The present invention relates to an improved composition that may be topically applied to infected areas of the epidermis which includes an animal fat combined with various natural herbs to form an ointment.

The present invention, the healing salve is comprised of a mixture of specific ingredients. Such ingredients in their broadest context include a fat and herbs. Such ingredients possess properties different from, or in addition to those possessed by the several ingredients in common and cooperate with respect to each other so as to attain the desired objective.

A new and improved healing salve for topical application to skin consisting essentially of fifty-five to seventy percent by weight of an animal fat having been extracted directly from the fatty tissue of an animal through heating; five to twenty percent by weight of a mixture of plantain; and five to ten percent by weight of a mixture of calendula.

The healing salve wherein the plantain being plantago major and plantago lancetowata. The healing salve having the ability to penetrate the human epidermis layer upon topical application for combating the infectious bacteria. The healing salve wherein the weight percent ratio between the animal fat and a mixture of the plantain and calendula is 7 to 2 to 1 or greater.

A method of making the healing salve comprises the steps of chopping a quantity of sheep fat into a plurality of small strips. Next grind together dried leaves of plantago major, plantago lancetowata and calendula and forming leaf pieces. Place the plurality of strips of sheep fat into a non metallic container and place the container over a heating element.

Turn the temperature of the heating element to about 100 degrees Celsius. The heating element is allowed to reached the desired temperature before placing the container of sheep fat on the element. The temperature of the element must be maintained at a constant temperature for frying of the sheep fat to a golden color. Once the desired golden color has been reached, remove the container from the heating element and let stand for about 5 minutes.

Once the standing time has been completed, add the pieces of leaves to the sheep fat and mix well. Cover the mixture with a lid and allow the mixture to remain in the container for about twenty-four hours. During the twenty-four hour period, the room temperature must not get higher than seventy degrees and no lower than fifty degrees.

The following example illustrates the invention:

EXAMPLE

A healing salve having the following composition of ingredients was prepared:

| components | | kg |
|---|---|---|
| Base | Animal fat | 2.2 kg |
| active agent | Plantago major | 3.5d kg |
| | Plantago lancetowanta | 3.5d kg |
| | Calendula | 3.5d kg |

These ingredients, after sitting for twenty-four hours, are heated. The mixture is heated until it liquefies. The liquid state of the mixture is passed through a press for collection into a container. The liquid, when pressed into a container, is allowed to become a cream. The cream, having been collected within the container and being covered with a lined lid, is stored in a cool place for later use.

The present composition of the healing salve is an ointment that has no toxins or chemical as ingredients. It is prepared only from natural herbs. The ointment, once formulated, must be refrigerated at all times and has a shelf life of one year. The health salve is for external use only and is applied to the infected area directly. The ointment is absorbed into the skin. The ointment may be used to cleanse the skin from the inside out and cures the infection.

The ointment, because of the fatty base material, retains the skins softness and moisture. The ointment may be used to fight off the bacteria or viral material that will cause any one of the following conditions: Athletics foot, mycosis, shingles, psoriasis, boils, hemorrhoids, acne, and atheroma. Additionally, when the healing salve is applied to bruised or swollen areas, it aides in the healing process of the bruised area and helps in the pain reduction of joints and knees that have fluid on them.

As to the manner of usage and operation of the present invention, the same should be apparent from the above description. Accordingly, no further discussion relating to the manner of usage and operation will be provided.

With respect to the above description then, it is to be realized that the optimum volume metrical relationships for the ingredients of the composition, to include variations amounts of components by weight of the entire composition and manner of intermixing are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A salve for topical application to skin consisting essentially of:

fifty-five to seventy percent by weight of an animal fat having been extracted directly from the fatty tissue of an animal through heating;

five to twenty percent by weight of a mixture of plantain lancetowata powder; the plantain further including five to twenty percent by weight a mixture of plantago major, and five to ten percent by weight of a mixture of calendula powder.

2. The salve as defined claim 1 having the ability to penetrate the human epidermis layer upon topical application for combating the infectious bacteria.

3. The salve defined in claim 1, wherein the weight percent ratio between the animal fat and a mixture of the plantain and calendula is 7 to 2 to 1 or greater.

4. A method of producing a salve, which comprises the steps of:

chopping a quantity of sheep fat into a plurality of small strips;

grinding together dried leaves of plantago major, plantago lacentowata and calendula with a grinding wheel and forming a powder;

placing the plurality of strips of sheep fat into a glazed metallic container and placing the container over a heating element;

raising the temperature of the heating element to about 100 degrees Celsius when the container having the plurality of strips contained therein, the heating element being maintained at a constant temperature for frying the plurality of strips therein until the strips obtain a golden color and a sheep fat being released;

removing the container having the strips therein from the heating element once the desired color being reached, and allowing the container with the colored strips therein to stand for about five minutes;

adding and mixing the powder to the sheep fat together in the container to form a mixture;

covering the mixture in the container with a lid and allowing the mixture to remain in the container for twenty-four hours at a room temperature no higher than seventy degrees and no lower than fifty degrees;

heating the mixture for the formation of a liquid after the twenty-four hour period having ended; and passing the liquid through a press for water removal from the liquid and collection into a glazed ceramic container where the liquid becomes a grease, the grease having been collected within the container and being covered with a lined lid for storing in a cool place for later use.

* * * * *

UNITED STATES PATENT AND TRADEMARK OFFICE
CERTIFICATE OF CORRECTION

PATENT NO. : 5,843,467
DATED      : December 1, 1998
INVENTOR(S): Wieslaw Ambroziewicz It is certified that error appears in the above-identified patent and that said Letters Patent is hereby corrected as shown below:

On the title page, line 2, please delete Ambroziewigz and insert therefor --Ambroziewicz--

Item [76] Inventor: please delete

Wieslaw Ambroziewigz, 23 Doncaster Drive, Brampton, Ontario, Canada, L6T 1S8 and insert therefor:

Wieslaw Ambroziewicz, 25 Haslemere Avenue, Brampton, Ontario, Canada, L6W 2X3

Signed and Sealed this

First Day of June, 1999

Attest:

Attesting Officer

Q. TODD DICKINSON

Acting Commissioner of Patents and Trademarks